United States Patent
Bastia et al.

(10) Patent No.: US 8,277,376 B2
(45) Date of Patent: Oct. 2, 2012

(54) PROCESS AND A DEVICE FOR SURGICAL TREATMENT OF RECTAL AND HAEMORRHOIDAL PROLAPSE

(75) Inventors: Filippo Bastia, Carpi (IT); Pier Paolo Dal Monte, Pianoro (IT)

(73) Assignee: THD S.p.A., Correggio (IT)

( * ) Notice: Subject to any disclaimer, the term of this patent is extended or adjusted under 35 U.S.C. 154(b) by 1133 days.

(21) Appl. No.: 11/814,666

(22) PCT Filed: Feb. 14, 2006

(86) PCT No.: PCT/IT2006/000074
§ 371 (c)(1),
(2), (4) Date: Jul. 24, 2007

(87) PCT Pub. No.: WO2007/094016
PCT Pub. Date: Aug. 23, 2007

(65) Prior Publication Data
US 2009/0259110 A1    Oct. 15, 2009

(30) Foreign Application Priority Data
Feb. 14, 2006   (IT) ..................... PCT/IT2006/000074

(51) Int. Cl.
*A61B 1/32* (2006.01)
*A61B 17/00* (2006.01)
(52) U.S. Cl. ........................................... 600/235
(58) Field of Classification Search .................. 600/114, 600/130, 136, 154, 184, 199, 235
See application file for complete search history.

(56) References Cited

U.S. PATENT DOCUMENTS

| | | | |
|---|---|---|---|
| 2,482,971 A | 9/1949 | Golson | |
| 3,701,347 A * | 10/1972 | Belkin | 600/184 |
| 4,527,553 A * | 7/1985 | Upsher | 600/188 |
| 4,819,620 A * | 4/1989 | Okutsu | 600/114 |

(Continued)

FOREIGN PATENT DOCUMENTS
JP    11-169342    6/1999
(Continued)

OTHER PUBLICATIONS

Kovanov V.V., "Operational Surgery and Topographic Anatomy", Medicine, Moscow, 1978, p. 176 (English translation of relevant extract).

(Continued)

*Primary Examiner* — Kevin T Truong
*Assistant Examiner* — Christopher Beccia
(74) *Attorney, Agent, or Firm* — Pearne & Gordon LLP

(57) ABSTRACT

A process for surgical operations on a rectal/haemorrhoidal prolapse comprises stages of realising, in the anal canal, at least a first circular stitching at a first portion of a haemorrhoidal prolapse; realising at least a second circular stitching in a second portion of the haemorrhoidal prolapse, and nearing the first circular stitching and the second circular stitching in order to create a constriction of the haemorrhoidal prolapse. The invention also relates to a device, preferably for actuating the process, which comprises a hollow divaricator (17) having a prevalent development direction along a longitudinal axis (Z) and being insertable in a patient's anal orifice. The device further exhibits a window (29) defining an operational area and creating a communication between a cavity (17b) internal of the divaricator (17) and a portion of haemorrhoidal prolapse. The device further comprises means for opening and closing (31) the window (29).

21 Claims, 3 Drawing Sheets

U.S. PATENT DOCUMENTS

| | | | |
|---|---|---|---|
| 5,741,273 A | 4/1998 | O'Regan | |
| 6,102,271 A | 8/2000 | Longo et al. | |
| 6,142,931 A * | 11/2000 | Kaji | 600/114 |
| 6,458,077 B1 * | 10/2002 | Boebel et al. | 600/154 |
| 6,595,917 B2 * | 7/2003 | Nieto | 600/223 |
| 6,974,466 B2 | 12/2005 | Ahmed et al. | |
| 7,029,438 B2 * | 4/2006 | Morin et al. | 600/184 |
| 7,037,314 B2 | 5/2006 | Armstrong | |
| 7,118,528 B1 | 10/2006 | Piskun | |
| 7,399,305 B2 | 7/2008 | Csiky et al. | |
| 7,494,038 B2 | 2/2009 | Milliman | |
| 7,611,458 B2 * | 11/2009 | Sias | 600/136 |
| 7,695,432 B2 * | 4/2010 | Scheyer | 600/184 |
| 7,731,654 B2 * | 6/2010 | Mangiardi et al. | 600/130 |
| 8,100,822 B2 | 1/2012 | Piskun | |
| 8,181,838 B2 | 5/2012 | Milliman et al. | |
| 2006/0155169 A1 * | 7/2006 | Bastia et al. | 600/199 |

FOREIGN PATENT DOCUMENTS

| | | |
|---|---|---|
| JP | 2001-286438 A | 10/2001 |
| WO | WO 01/21060 | 3/2001 |
| WO | WO 0121060 * | 3/2001 |
| WO | WO 2004/064624 | 8/2004 |

OTHER PUBLICATIONS

Morinaga K, et al., "A Novel Therapy for Internal Hemorrhoids Ligation of the Hemorrhoidal Artery With a Newly Devised Instrument (Moricorn) in Conjunction With a Doppler Flowmeter", Am. J. Gastroentrol, vol. 90 No. 4, Apr. 1995, pp. 610-613 (English abstract).

Boguslavskaya, T.B., et al., "Mastering of the Operational Technique Elements—Disconnection and Connection of Soft Tissues. Temporal and Permanent Hemostasis in an Operational Wound", General Surgical Instruments and Suturing Material, Moscow, 1995, p. 23, Fig. 30 (English translation of relevant extract).

Schwabe Catalogue, Moscow, 1901, p. 419.

* cited by examiner

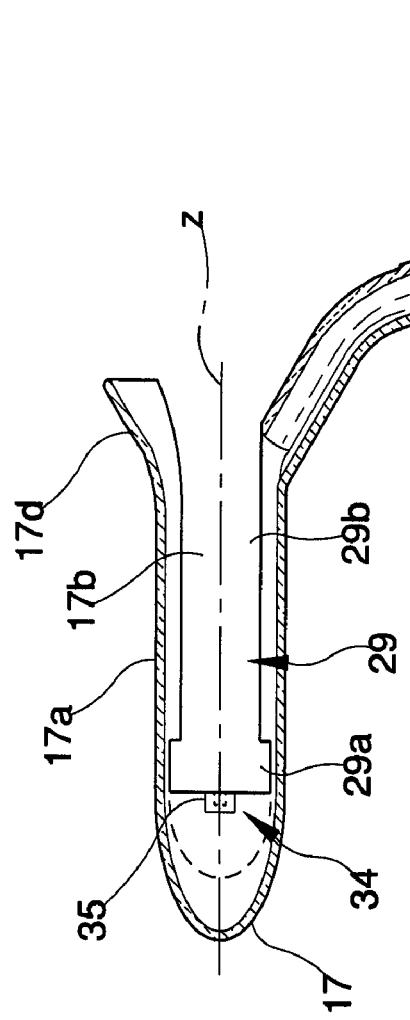
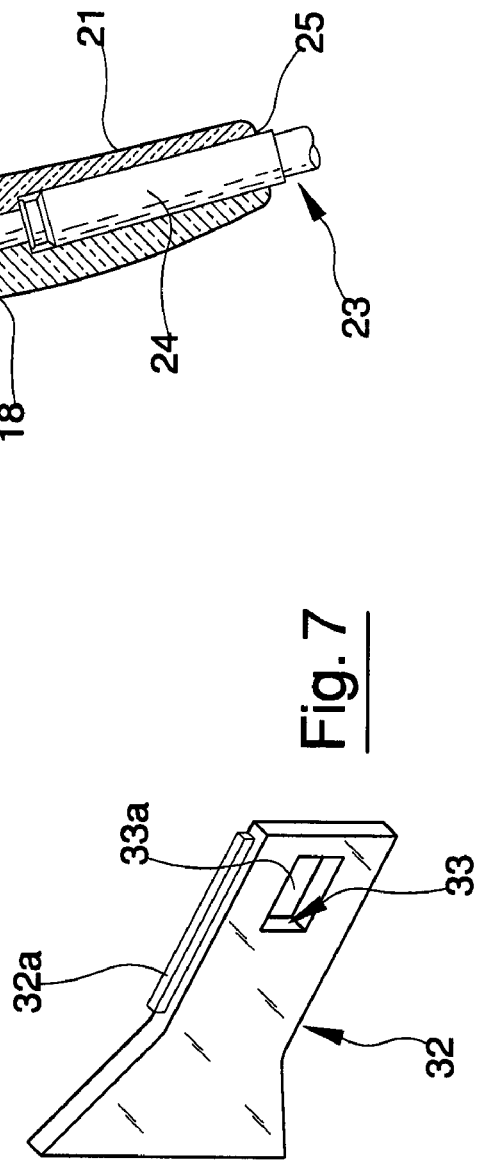
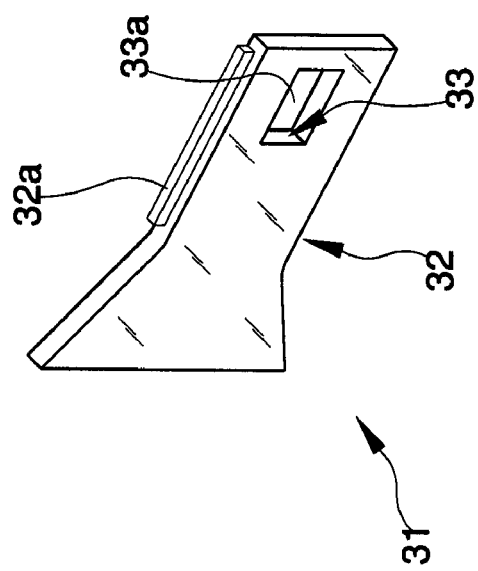

PROCESS AND A DEVICE FOR SURGICAL TREATMENT OF RECTAL AND HAEMORRHOIDAL PROLAPSE

TECHNICAL FIELD

The invention relates to a process and a device for surgical treatment of rectal and haemorrhoidal prolapse.

The invention applies to the field of surgical operations associated to proctological pathologies, in particular aimed at treatment and/or reduction of rectal and haemorrhoidal prolapse.

BACKGROUND ART

As is well-known, the development of haemorrhoidal diseases is caused by pathological alterations in the cavities of the anal canal, which are formed by vascular spaces, arteriovenous shunts and saccular venous structures constituting the internal haemorrhoidal plexus. In more detail, the internal haemorrhoidal plexi are haematic spaces of a calibre of a few millimetres delimited by a venous or capillary endothelium internal of a connective tissue, covered by rectal mucous membrane. These structures are supported by anchoring fibres to the internal sphincter, which form the Treitz or Parks ligaments.

The cavities receive arterial flow only from terminal branches of the upper rectal artery, a peculiarity which has led to the treatments adopted for the most recent treatment programmes.

The development of surgical techniques in this field is in continual evolution, as where possible it is sought to render these operations as little traumatic as possible, especially in the light of the prior art, which often leads to grave risks and complications for patients who are subjected to this type of operation.

The principal surgical techniques, especially with reference to the past, were based on the removal of tissue, i.e. the surgical removal of the portions of rectal mucous membrane affected by the pathology.

A procedure of this type includes the removal of haemorrhoidal prolapses at the same time as suturing the interested areas.

A procedure of this type is described in detail in document WO 01/21060, which illustrates an accessory kit for trans-anal operations, and a procedure for use thereof.

In detail, this procedure involves acting on the mucous wall of the rectal wall, especially on the portion of mucous wall interested by the haemorrhoidal prolapse, by providing a ring or circumferential structure, similar to a tobacco pouch. This is done by circular stitching a suture thread several times until it interests the whole prolapse along the circumferential development of the rectal ampoule, realising an annular extrusion which tends towards the inside of the rectal ampoule.

Subsequently the annular extrusion thus realised is resected, simultaneously suturing the remaining bunched edges of the mucous wall.

A device used for realising this procedure comprises a semi-cylindrical body, coupled to a handle that can be gripped and inserted into the anal orifice of a patient, for example using an anatomical cone-shaped introducer. The semicylindrical body exhibits an opening at a front end thereof, which intercepts a part of the haemorrhoidal prolapse and enables extrusion thereof internally of the body. The device further comprises a mechanical suturing device, used after the semicylindrical body, for cutting the annular extrusion by means of a cylindrical blade, and suturing the closed-to edges of the remaining part of the mucous membrane by firing metal staples internally of the edges.

A procedure of this type is necessarily very traumatic.

In particular, though giving good results and on the whole preventing relapses, the procedure causes considerable post-operative pain, and requires admission of the patient to hospital and can also be the cause of greater post-operative and intra-operative risks.

Different intervention techniques have also been researched, known as para-surgical techniques, aimed at obviating the grave drawbacks of traditional surgery. These techniques comprise, for example, elastic ligation of the haemorrhoidal tissue, compressing a haemorrhoid at its point of attachment to the mucous wall of the rectal canal by elastic ligature, and causing the physiological collapse thereof without recourse to excision of the haemorrhoidal tissue. A further example of para-surgical technique is sclerotherapy, which causes necrosis of the interested part by injection of a sclerosing solution.

Further examples of para-surgical techniques comprise infra-red coagulation, cryotherapy or laser therapy.

Some of these para-surgical treatments adopt a device of the type described in patent WO 2004/064624. This device comprises a cylindrical body functioning as a divaricator, exhibiting a grip and, in the lateral position, an opening for intercepting and observing a portion of haemorrhoidal prolapse. In proximity of the opening, the body comprises a seating for housing a probe (in particular, an ultrasound probe) able to detect vicinity to a blood vessel in order to enable a correct direct intervention on the zone actually interested by the haemorrhoidal prolapse, even where there is a poor visibility and/or accessibility to the area. The device further comprises means for illuminating, associable to the grip, for illuminating the area interested by the intervention and if necessary for lighting up the inside of the cylindrical body. In particular, a device of the above-described type is used for creating the surgical occlusion in the terminal part of the upper rectal artery, which involves the haemorrhoidal prolapse, by a ligature in the area surrounding the artery (with the use of a curved suturing needle) followed by a pinching of the area causing collapse due to interruption of blood flow.

However, this technique cannot by itself reduce, over a short time period, the presence of the haemorrhoidal prolapse internally of the anal canal.

Therefore a technical aim of the present invention is to provide a process and a device for surgical operations on a rectal and a haemorrhoidal prolapse which obviates the above-cited drawbacks.

A fundamental aim of the invention is to provide a process and a device for surgical operations on a rectal and a haemorrhoidal prolapse which reduces haemorrhoidal prolapses internally of the rectal canal in a short time.

A further aim of the invention is to provide a process and a device for surgical operations on a rectal and haemorrhoidal prolapse which is able to reduce post-operative complications and post-operative pain.

A further important aim of the invention is to provide a process and a device for surgical operations on a rectal and haemorrhoidal prolapse which limits a need for using anaesthetics on the patient, or which in any case localises the need for anaesthesia as far as possible.

The specified aims and others besides are substantially attained by a process and device for surgical operations on a rectal and haemorrhoidal prolapse according to what is set out in the appended claims.

DISCLOSURE OF INVENTION

A description will now be made, by way of non-exclusive and non-limiting example, of a preferred embodiment of a process and a device for surgical operations on a rectal and haemorrhoidal prolapse, with reference to the accompanying figures of the drawings, in which:

FIG. 5 is a section view of a first portion of the device of FIG. 2;

FIG. 6 is a lateral view of a second portion of the device of FIG. 2;

FIG. 7 is a perspective view of a second portion of the device of FIG. 2.

Figure 1:
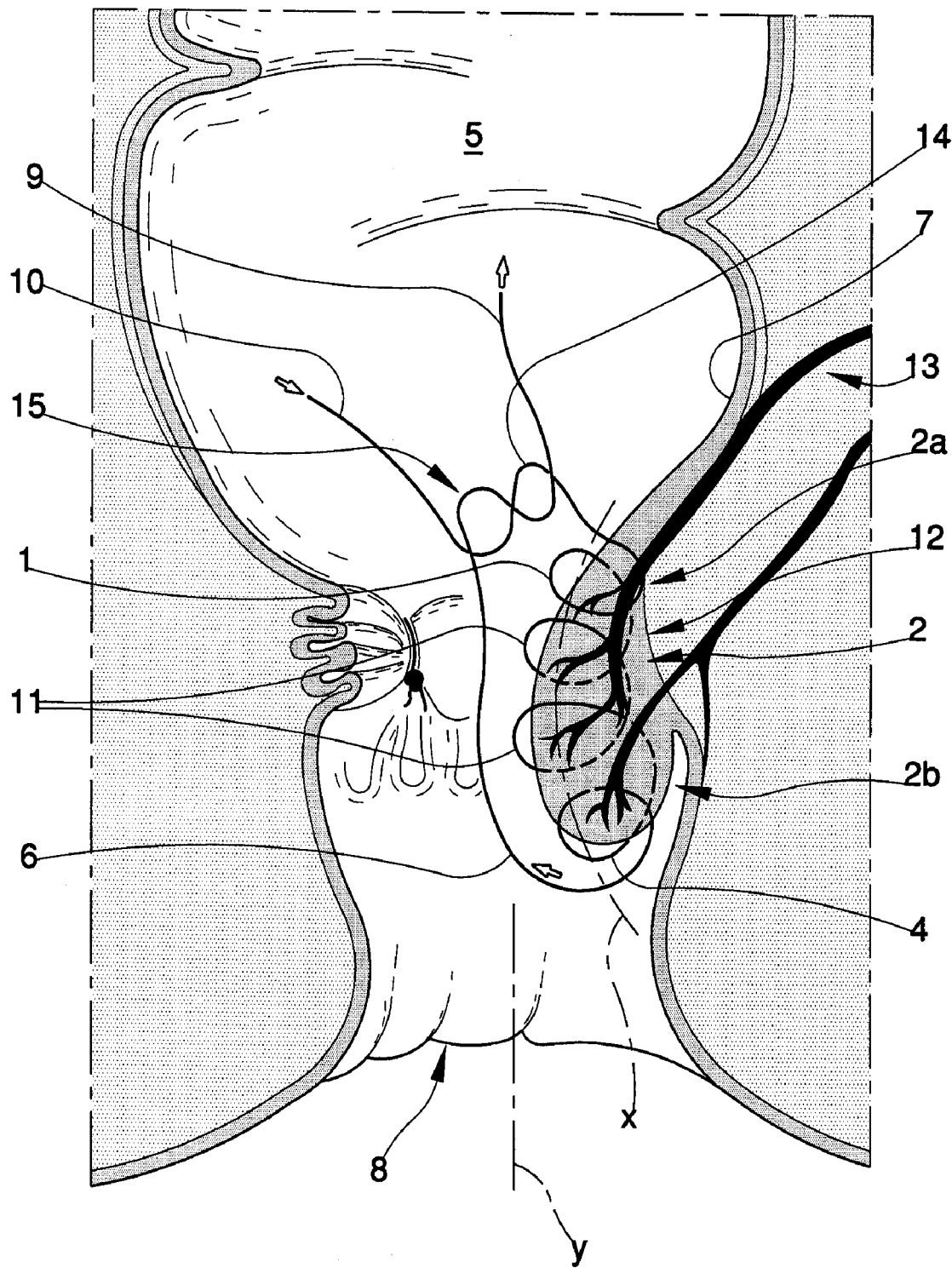
FIG. 1 is a schematic view in longitudinal section of an anal canal.

A preferred embodiment of a process and a device for surgical operations on a rectal and haemorrhoidal prolapse of the invention comprises the following stages:

realising at least a first circular stitching 1 at a position of a rectal-haemorrhoidal prolapse 2 by means of, for example, a suture thread 6;

realising at least a second circular stitching 4 at the same position i.e. at the haemorrhoidal prolapse 2 nearing the first 1 and second 4 circular stitchings in order to create a constriction of the haemorrhoidal prolapse 2.

Advantageously the first circular stitching 1 and the second circular stitching 4 are made respectively at a first portion 2a and a second portion 2b of the haemorrhoidal prolapse 2, which is localised, in FIG. 1, in proximity of the end of terminal tract of the rectum 5 and develops in a prevalent direction X. Further, the first portion 2a of the prolapse 2 is deeper inside the rectum 5 than the second portion 2b. This gives special advantages, as will better emerge in the following description.

The circular stitchings are made using various suturing elements.

In the embodiment of FIG. 1, a thread 6 is preferred and illustrated, which will be termed hereinafter the suturing thread 6.

The suturing thread 6 is wound several times about the haemorrhoidal prolapse 2, which projects from a wall 7 of the rectum 5 towards the inside of the rectum 5 itself and in the direction of the anal orifice 8 of the rectum 5. In the schematic illustration of FIG. 1, the wire 6 is partially inserted internally of the tissues which constitute the wall 7 of the rectum 5, and in particular internally of the tissues defining the haemorrhoidal prolapse 2. The insertion of the thread 6 in the tissues is preferably done using an acuminate body, for example a needle, not illustrated as of known type.

Preferably the stage of realisation of the first circular stitching 1 is done by inserting a first end 9 of the thread 6 into the first portion 2a of the haemorrhoidal prolapse 2. The realisation of the second circular stitching 4, preferably using the same suture thread 6, is done in the same way, by inserting the first end 9 of the thread 6 into the second portion 2b of the haemorrhoidal prolapse 2. The thread 6, in this configuration and as in FIG. 1, exhibits the first end 9 at the position of the second circular stitching 4, while it exhibits a free second end 10 at the position of the first circular stitching 1. The above-described process has the curved needle at the first end of the thread 6.

The stage of realising the first circular stitching 1 advantageously also comprises a stage of realising further circular stitchings 11. The further circular stitchings 11 are realised at a third portion 12 of the haemorrhoidal prolapse 2, situated between the first portion 2a and the second portion 2b. FIG. 1 illustrates two further circular stitchings 11, located in intermediate positions between the first circular stitching 1 and the second circular stitching 4. The circular stitchings 1, 4, 11 are preferably realised using a single suture thread 6.

Furthermore, each circular stitching 1, 4, 11 of the thread 6 advantageously interests a terminal branch of a rectal artery 13 associated to the haemorrhoidal prolapse 2, with the result that the terminal branch can subsequently be pinched, following a technique which will be described herein below.

In particular, the curved needle is handled and guided to complete a track, internally of the tissues of the haemorrhoidal prolapse 2, which circumscribes the terminal branch of the rectal artery 13 so that at the end, when the curved needle re-emerges from the tissues, a loop is generated, internally of which the above-mentioned rectal artery 13 terminal branch is contained. Thus each stage of realisation of a circular stitching 1,4, 11, comprises a stage of realising at least a loop linked to the terminal branch of the rectal artery 13 interested by the proctological pathology.

In the preferred embodiment of the process of the invention and illustrated in FIG. 1, each loop is contained in a plane which is perpendicular to the prevalent development direction X of the haemorrhoidal prolapse 2. This is advantageous as each stage of the realisation of a circular stitching 1, 4, 11 also comprises a stage of pinching the respective circular stitching 1,4, 11. Each single loop, once completed, is subjected to a preferably manual drawing action on the suture thread 6. This is much simplified by the lie of the single loops as described above, as an exclusively transversal constriction is realised with respect to the development of the rectal artery 13, without causing alterations in an axial direction.

The drawing of the suture 6 has the aim of realising a constriction of a portion of the haemorrhoidal prolapse 2 (and therefore a respective tract of the rectal artery 13) associated to a single loop, and causes interruption of blood flow in that tract, leading to collapse thereof.

The stages of creating the circular stitchings 1, 4, 11 are preferably performed by realising the circular stitchings 1, 4, 11 in substantially overlapped positions along the prevalent development direction X of the haemorrhoidal prolapse 2. This results in an ordered succession of loops according to the configuration of FIG. 1, in which a single loop "packet" orderedly surrounds the haemorrhoidal prolapse 2.

Subsequently to the completion of the circular stitchings 1, 4, 11 stages, advantageously there is a stage of reciprocal nearing of the first circular stitching 1 and the second circular stitching 4 in order to realise a constriction of the haemorrhoidal prolapse 2 also along its prevalent development direction X. In this way a considerable reduction of the overall size of the haemorrhoidal prolapse 2 internally of the rectum 5 is achieved.

The stage of nearing the circular stitchings 1, 4 is preferably done via a stage of knotting the suture thread 6. The knotting stage comprises a stage of realising one or more consecutive knots, which stabilise a preceding nearing action of the circular stitchings 1, 4.

Further, the process of the invention can advantageously comprise a stage of creating a further circular stitching, in particular the "basic circular stitching", partially illustrated in FIG. 1 and denoted by 14, which serves as a reference for the final drawing-in of the thread 6.

This stage, preferably performed before realising the first circular stitching 1, is done by creating at least a loop in a portion of wall of the rectum 5 which is not involved in the haemorrhoidal prolapse 2. The realisation of the basic circular stitching 14 has the aim of defining an anchor for the subsequent stage of nearing the circular stitchings 1, 4, as will be better explained herein below.

It is further preferable that the basic circular stitching 14 be realised using the suture thread 6 used for realising the circular stitchings 1, 4, 11. The basic circular stitching 14 is further realised preferably in a portion of the rectum 5 situated more deeply than the haemorrhoidal prolapse 2 with respect to the anal orifice 8, and thus in a higher position as in FIG. 1. The basic circular stitching 14 is thus situated more deeply than the first circular stitching 1 too, by virtue of what is stated herein above with reference to the directing of the first circular stitching 1 and the second circular stitching 4.

In detail, the second end 10 of the suture thread 6, localised at the first circular stitching 1 and therefore at the basic circular stitching 14 position, is partially folded in order to define a slot, denoted by 15 in FIG. 1 in an initial stage of formation. The first end 9 of the suture thread 6 can be inserted internally of the slot 15 and the stage of nearing the circular stitchings 1, 4 can begin, by drawing the suture thread 6; then the knotting stage can be begun, which defines a stable nearing position of the circular stitchings.

The above stages, which constrict the haemorrhoidal prolapse 2, also raise the haemorrhoidal prolapse 2 in the direction of the basic circular stitching 14 and deep into the anal canal 5 (as can be seen on the area on the right of FIG. 1 which illustrates the constriction and raising of a treated haemorrhoidal prolapse 2). This gives the advantage of distancing the haemorrhoidal prolapse 2 from the anal orifice 8, reducing its size internally of the rectum 5 and also correctly repositioning the anal padding above the pain threshold line.

The basic circular stitching 14 therefore functions as a point of reference, towards which the haemorrhoidal prolapse 2 is pulled and then linked with the circular stitchings 1, 4, 11 so as to generate at the same time the constriction of the haemorrhoidal prolapse 2 and the reduction of the size of the haemorrhoidal prolapse 2 internally of the rectum 5.

The process of the invention is applicable to operations for haemorrhoidal prolapses of various types and entities, and can be summed up by being described as including the creation of a plurality of circular stitchings able to link the haemorrhoidal prolapse and the associated rectal artery, preferably by means of a single suture thread and the realisation of at least one basic circular stitching, made at a portion of the rectal canal wall which is not interested by haemorrhoidal pathologies.

There follows a description of a device for surgical operations on a rectal-haemorrhoidal prolapse, preferably but not exclusively for realising the above-described process.

The device, denoted by 16, comprises a hollow divaricator 17, exhibiting a cylindrical central portion 17a internally affording a cavity 17a which is the intervention zone of the device. The central portion 17a is connected to a closed front portion 17c having a preferably tapered cone shape to enable it to be inserted internally of the anal orifice of a patient, reducing to a minimum the patient's traumatic experience. The divaricator 17 further comprises a truncoconical posterior portion 17d, larger transversally in order to define the maximum penetration of the divaricator 17 internally of the anal orifice. The posterior portion 17d is also hollow, to afford access to the cavity 17b by an external operator during an operation, at a posterior end 17e with reference to a penetration direction of the divaricator 17 internally of the anal orifice.

The device 16 further comprises a first half-shell 18, firmly constrained to the posterior portion 17c of the divaricator 17 to form a handle portion of the device 16. The first half-shell 18 is coupled, preferably by male-female jointed parts 19, 20, to a second half-shell 21, which completes the formation of the handle of the device 16. In this configuration, the handle defines, in a portion comprised between the two half-shells 18, 21, a first seating 22 for housing means for illuminating 23.

The means for illuminating 23 are preferably made with an optic fibre 24. The optic fibre 24 is, for example, inserted at a free end of the handle, pushed internally of the first seating 22 up until it reaches an operative position in which it emits a light which can reach inside the divaricator 17 in order to illuminate the work area (retro-illumination).

The divaricator 17 exhibits, preferably in a lateral portion thereof, a window 29 which defines an area of operation and which establishes a communication between the cavity 17b, and therefore the means for operating positioned internally of cavity 17b, and a wall of the rectum, when the device 16 is inserted. The window 29 enables easy access to a haemorrhoidal prolapse present on the rectum wall.

Figure 2:
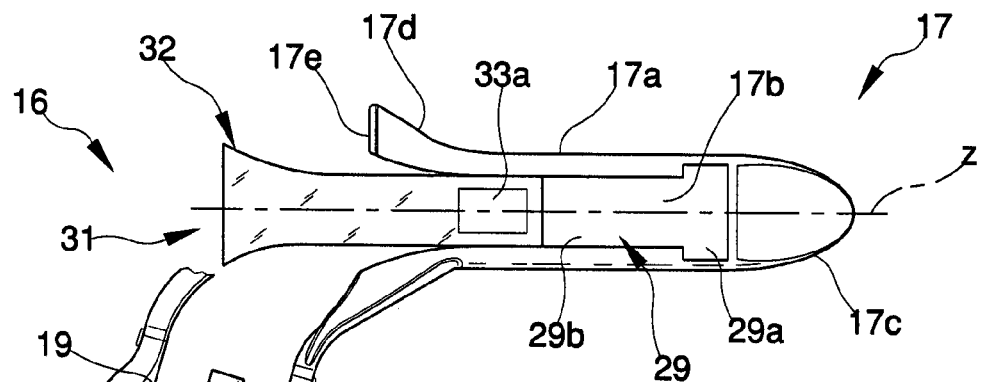
FIG. 2 is a lateral view of a device of the invention.
Figure 3:
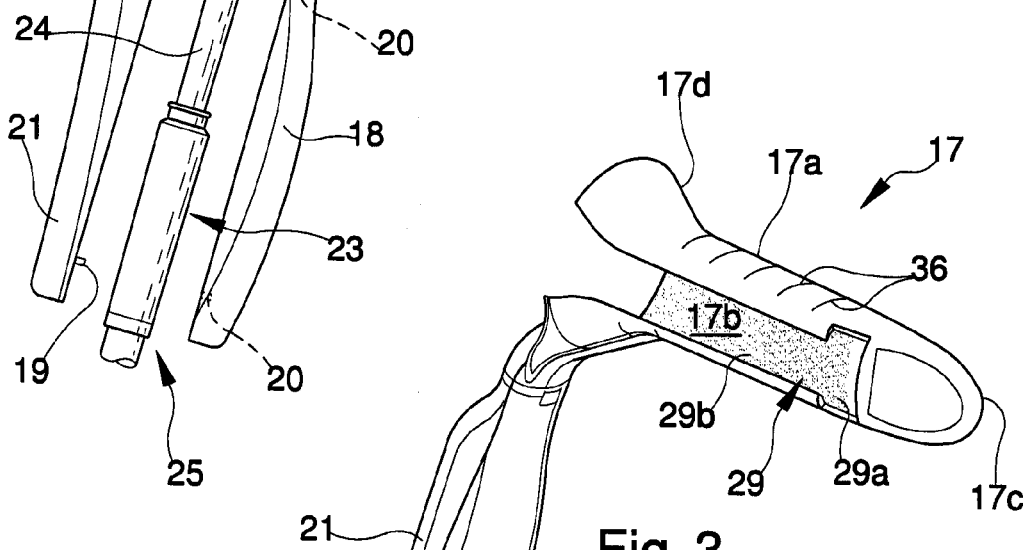
FIG. 3 is a perspective view of a first portion of the device of FIG. 2.
Figure 4:
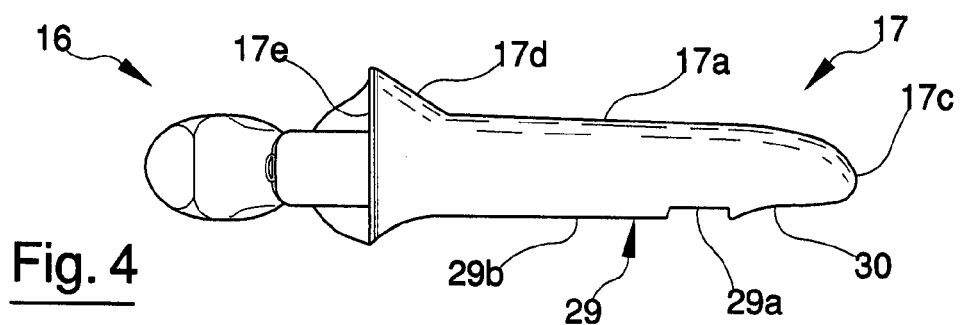
FIG. 4 is a plan view of a first portion of the device of FIG. 2.

The window 29 exhibits at least a first portion 29a, between the central portion 17a and the front portion 17c. In the preferred embodiment illustrated in FIGS. 2 and 3, the first portion 29a of the window 29 extends prevalently in a transversal direction to a longitudinal axis Z, along which longitudinal axis Z the divaricator 17 prevalently develops. In the illustrated embodiment, the first portion 29a of the window 29 is rectangular.

Preferably the front portion 17c of the divaricator 17 exhibits, in proximity of the first portion 29a of the window 29, a bevel 30 for further facilitating penetration of the divaricator 17 internally of the anal orifice, while at the same time the bevel 30 receives the haemorrhoidal prolapse in the window 29.

The window 29 advantageously has a variable extension, preferably in a parallel direction to the longitudinal axis Z of the divaricator 17. This extensibility is achieved by means for opening and closing 31 the window 29, which means will be better explained herein below.

The window 29 advantageously exhibits a second portion 29b, preferably adjacent to the first portion 29a. In the preferred embodiment, the first portion 29a and the second portion 29b are in communication, and thus constitute a single window 29. Further, the second portion 29b of the window 29 develops along the longitudinal axis Z of the divaricator 17 and extends preferably from the first portion 29a up to the posterior end 17e of the divaricator 17. The second portion 29b can have any transversal size, preferably less than or equal to the transversal size of the first portion 29a.

The means for opening and closing 31 the window are preferably realised using a mobile wall 32. The mobile wall 32 is slidably housed in the second portion 29b of the window 29, for example by means of sliding guides 32a, and can take on a plurality of operative positions between a closed position, in which it entirely obstructs the second portion 29b of the window, leaving accessible only the first portion 29a, and an open position, in which is completely discovers the second portion 29b of the window 29, which is thus entirely open and accessible from the outside. The mobile wall 32 is moved between the closed and open positions by a sliding motion in the direction of the posterior end 17e of the divaricator 17. The increase in extension of the window in the longitudinal direction as described above is advantageous especially when performing ligature operations on the rectal artery is stitched, in a haemorrhoidal pathology.

In a preferred embodiment, illustrated in the accompanying figures of the drawings, the mobile wall 32 is associated only to the second portion 29b of the window 29, while the first portion 29a is accessible from the outside even when the mobile wall 32 is in the closed position.

The mobile wall 32 can further exhibit dedicated means for gripping so that the operator has an easy grip thereon. In the preferred and illustrated embodiment, however, the mobile wall 32 is counter-shaped to the second portion 29b of the window 29 with which it engages, so that in the closed position there is no projection of the mobile wall 32 with respect to the normal surface progression of the divaricator 17.

The device 16 also comprises sensors, not illustrated, for detecting the pulsation of a vein or artery, in particular for detecting the vicinity of a rectal artery. The sensors are preferably an ultrasound probe, and can advantageously be housed on the mobile wall 32, preferably removably, so as continuously to monitor the vicinity of the rectal artery even during the sliding motion of the mobile wall 32.

For housing the sensors the mobile wall 32 exhibits a dedicated housing 33 facing towards an outside of the mobile wall 32 and therefore the divaricator 17, by means of an external terminal aperture 33a afforded on the mobile wall 32. The external terminal opening 33a, which places the housing 33 in communication with the outside of the divaricator 17, facilitates detection of the rectal artery by the sensors, bringing them up to the wall of the rectum and placing them in direct contact with the haemorrhoidal prolapse, so that they can detect the proximity of the artery by registering the associated blood flow. The housing 33 is preferably also in communication with the cavity 17b of the divaricator 17 to enable introduction of the sensors internally of the housing 33 through the posterior end 17e of the divaricator 17.

Means for guiding 34 are housed internally of the cavity 17b, which means for guiding are fixed to the divaricator 17 and destined to guide the means for operating during use, i.e. during the operating stage. In more detail, the means for guiding 34 comprise a holed support 35, preferably positioned in proximity of the first portion 29a of the window 29. Further, the holed support 35 is fixed in a non-centred position in proximity of the first portion 29a of the window 29. Further, the holed support 35 is fixed in a non-centred position with respect to the longitudinal axis Z of the divaricator 17, in particular towards the window 29. This is very useful for the arterial ligature operations, in which a curved needle gripped by a needle holder is made to describe a circular trajectory so that the needle, partially exiting from the divaricator 17 through the window 29, links the interested haemorrhoidal artery, previously detected by the ultrasound probe. The circular trajectory is obtained by causing the needle holder to rotate, while a front end thereof is housed internally of the holed support 35.

Externally the divaricator 17 can exhibit, at least on the central portion 17a thereof, one or more easily visible calibration marks 36, which can be for example a plurality of reliefs, to give an intuitive indication of the depth of penetration of the divaricator 17 into the anal orifice in real time.

The invention offers important advantages.

Primarily, the described process rapidly reduces the haemorrhoidal prolapse, preventing the need for painful surgical operations.

Further, the process involves less need for anaesthesia in comparison to traditional treatments.

Among the advantages of the process, first and foremost is the excellent results it obtains with haemorrhoidal pathologies, while preserving the vascular padding which is important for questions of continence.

A further advantage is given by the fact that the process, thanks to the anchoring of the haemorrhoidal prolapse to the basic circular stitching, enables repositioning of the anal padding above the pain threshold line, thus eliminating the haemorrhoidal prolapse.

Regarding the described device, an important advantage is given by the presence of the detractable mobile wall, which facilitates modification of the area of operation, preferably in a case of arterial ligature operations, without having even to partially extract the divaricator, which is a particularly laborious task for the surgeon.

Further, the fixing of the sensor on the mobile wall enables a continuous checking on the proximity of the interested rectal artery, without having to move the device if not strictly necessary.

Finally, the special geometry of the mobile wall does not include any projecting element able to cause discomfort or pain to the patient; indeed, the regular and anatomical shape of the wall satisfies the requirement for a low level of patient trauma.

The invention claimed is:

1. A device for surgical operations on a rectal or haemorrhoidal prolapse, comprising a hollow divaricator extending along a longitudinal axis and being insertable in an anal orifice, the divaricator exhibiting a window defining an operation area and providing a communication between an internal cavity of the divaricator and a portion of a haemorrhoidal prolapse, the window comprising a first portion and a second portion, the second portion extending parallel to the longitudinal axis, the first portion protruding relative to the second portion in a direction which is transverse to the longitudinal axis, the device further comprising a mobile wall effective for opening and partially closing the window to change the operation area, the mobile wall being non-rotatable around the longitudinal axis and being slidable in a direction parallel to the longitudinal axis so that the mobile wall can open and close the second portion but cannot close the first portion.

2. The device of claim 1, wherein the mobile wall is slidably coupled to the divaricator.

3. The device of claim 1, wherein the mobile wall is positionable in a plurality of operative positions between a closed position, in which the mobile wall completely obstructs the second portion of the window, and an open position, in which the second portion of the window is completely open.

4. The device of claim 1, wherein the second portion of the window extends from the first portion of the window up to a posterior end of the divaricator, the posterior end being defined by an insertion direction of the divaricator into the anal orifice.

5. The device of claim 2, wherein the device further comprises sliding guides for slidably coupling the mobile wall to the divaricator.

6. The device of claim 2, wherein the mobile wall comprises a housing for removably housing a sensor for detecting a proximity of a haemorrhoidal artery.

7. The device of claim 6, wherein the mobile wall comprises an external terminal opening for bringing the sensor close up to the haemorrhoidal artery.

8. The device of claim 6, wherein the housing realised in the mobile wall is in communication with the cavity of the divaricator, for facilitating insertion and fixture of the sensor on the mobile wall, operating directly from the cavity.

9. The device of claim 1, wherein the device further comprises a grip, fixed to the divaricator, the grip comprising a pair of coupled half-shells, the grip internally affording a first seating for housing a means for illuminating.

10. The device of claim 1, wherein the device further comprises means for guiding, fixed to the divaricator internally of the cavity for guiding means for operating during use thereof in an operating stage.

11. The device of claim 1, wherein the divaricator comprises a front portion, with respect to an insertion direction of the divaricator internally of the anal orifice, which front portion is closed and cone-shaped for facilitating insertion of the divaricator into the anal orifice.

12. The device of claim 1, wherein the divaricator externally exhibits a plurality of calibration marks for evidencing a depth of penetration of the divaricator internally of the anal orifice.

13. The device of claim 1, wherein said first portion of the window is rectangular.

14. The device of claim 1, wherein said first and second portions are in communication and constituting a single window.

15. The device of claim 1, wherein the mobile wall is slidably housed in the second portion of the window and can assume a plurality of operative positions between a closed position, in which the mobile wall entirely obstructs the second portion of the window leaving accessible only the first portion of the window, and an open position, in which the mobile wall completely uncovers the second portion of the window which results in the second portion being entirely open and accessible from outside.

16. The device of claim 15, wherein the first portion of the window is accessible from outside even when the mobile wall is in the closed position.

17. The device of claim 15, wherein the mobile wall is counter-shaped to the second portion of the window with which it engages, so that in the closed position there is no projection of the mobile wall with respect to a normal surface progression of the divaricator.

18. A device for surgical operations on a rectal or haemorrhoidal prolapse, comprising a hollow divaricator extending along a longitudinal axis and being insertable in an anal orifice, the divaricator exhibiting a window defining an operation area and providing a communication between an internal cavity of the divaricator and a portion of a haemorrhoidal prolapse, the device further comprising a mobile wall effective for opening and partially closing the window to change the operation area, the mobile wall being non-rotatable around the longitudinal axis and being slidable in a direction parallel to the longitudinal axis, wherein the mobile wall comprises a housing for removably housing a sensor for detecting a proximity of a haemorrhoidal artery.

19. The device of claim 18, wherein the mobile wall comprises an external terminal opening for bringing the sensor close up to the haemorrhoidal artery.

20. The device of claim 18, wherein the housing realised in the mobile wall is in communication with the cavity of the divaricator, for facilitating insertion and fixture of the sensor on the mobile wall, operating directly from the cavity.

21. The device of claim 18, wherein said sensor is removably housed on the mobile wall.

* * * * *